United States Patent [19]
Jhuboo et al.

[11] Patent Number: 5,242,408
[45] Date of Patent: Sep. 7, 1993

[54] METHOD AND APPARATUS FOR DETERMINING PRESSURE AND DETECTING OCCLUSIONS IN A SYRINGE PUMP

[75] Inventors: Nasser Jhuboo, St. Etienne de St. Geoirs; Jean-Claude Rondelet, St. Etienne de Crossey, both of France

[73] Assignee: Becton, Dickinson and Company, Franklin Lakes, N.J.

[21] Appl. No.: 950,377

[22] Filed: Sep. 23, 1992

[51] Int. Cl.$^5$ ............................................. A61M 1/00
[52] U.S. Cl. ..................................... 604/152; 604/121; 604/67
[58] Field of Search ................. 604/131, 151, 152, 49, 604/67, 118, 121, 207; 128/DIG. 12

[56] References Cited

U.S. PATENT DOCUMENTS

| | | | |
|---|---|---|---|
| 4,322,201 | 3/1982 | Archibald | 604/152 |
| 4,460,355 | 7/1984 | Layman | 604/121 |
| 4,747,828 | 5/1988 | Tsco | 604/121 |
| 4,836,752 | 6/1989 | Burkett | 604/152 |
| 4,898,579 | 2/1990 | Groshoug et al. | 604/152 |
| 5,047,012 | 9/1991 | Leuschner et al. | 604/152 |

FOREIGN PATENT DOCUMENTS 0319648 7/1988 European Pat. Off. .

*Primary Examiner*—John G. Weiss
*Attorney, Agent, or Firm*—Michael G. Schwarz

[57] ABSTRACT

A syringe pump is disclosed in which the pressure in the syringe is monitored. The syringe pump includes a force detector which detects the force on the plunger of the syringe. The force on the plunger of the syringe is converted into a force by means of an algorithm which is independent of the cross-sectional area of the syringe. The algorithm calculates the pressure by subtracting a predetermined frictional force from the measurement force and multiplying the result by a calibration pressure divided by the difference between a calibration force and the predetermined frictional force.

8 Claims, 9 Drawing Sheets

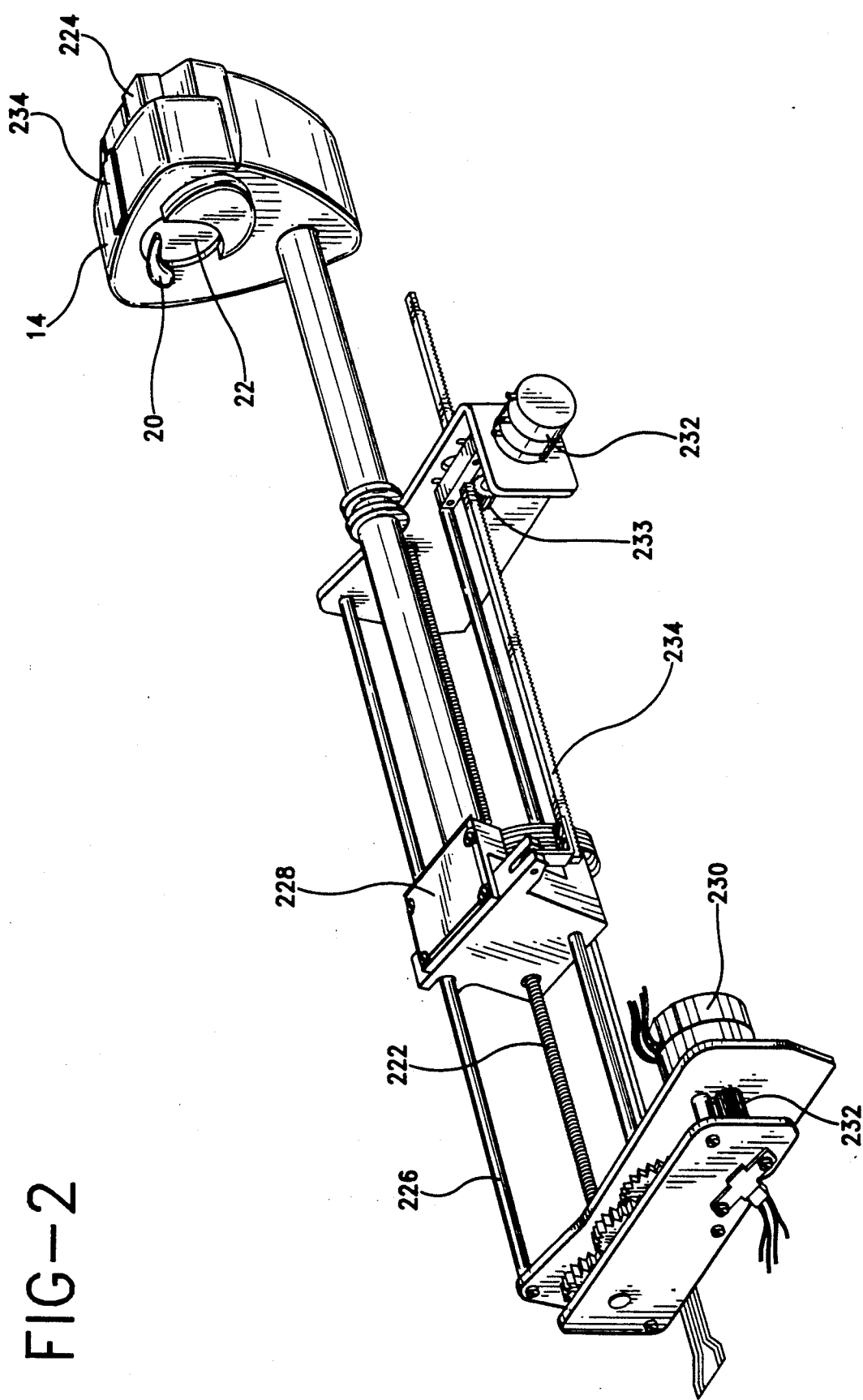

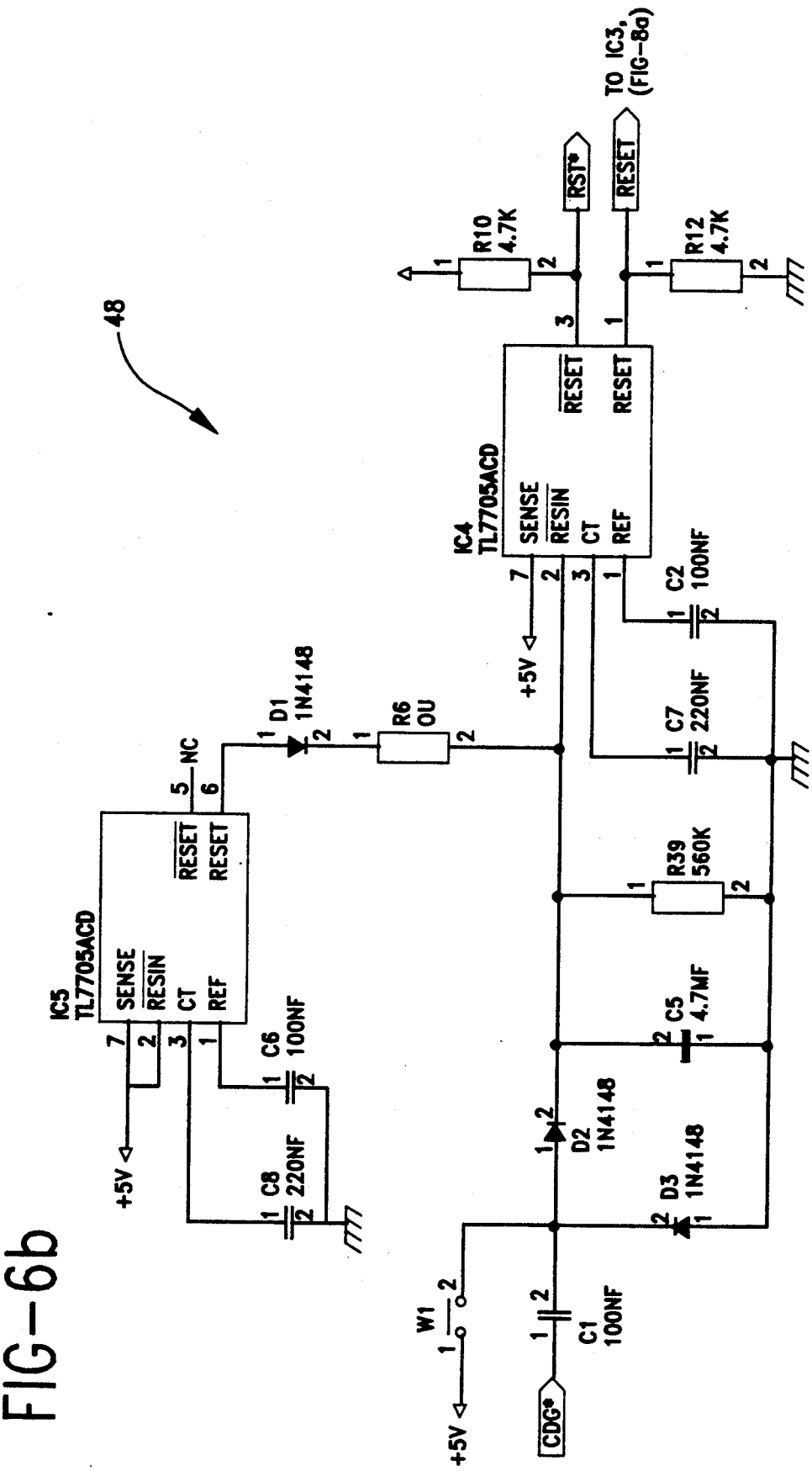

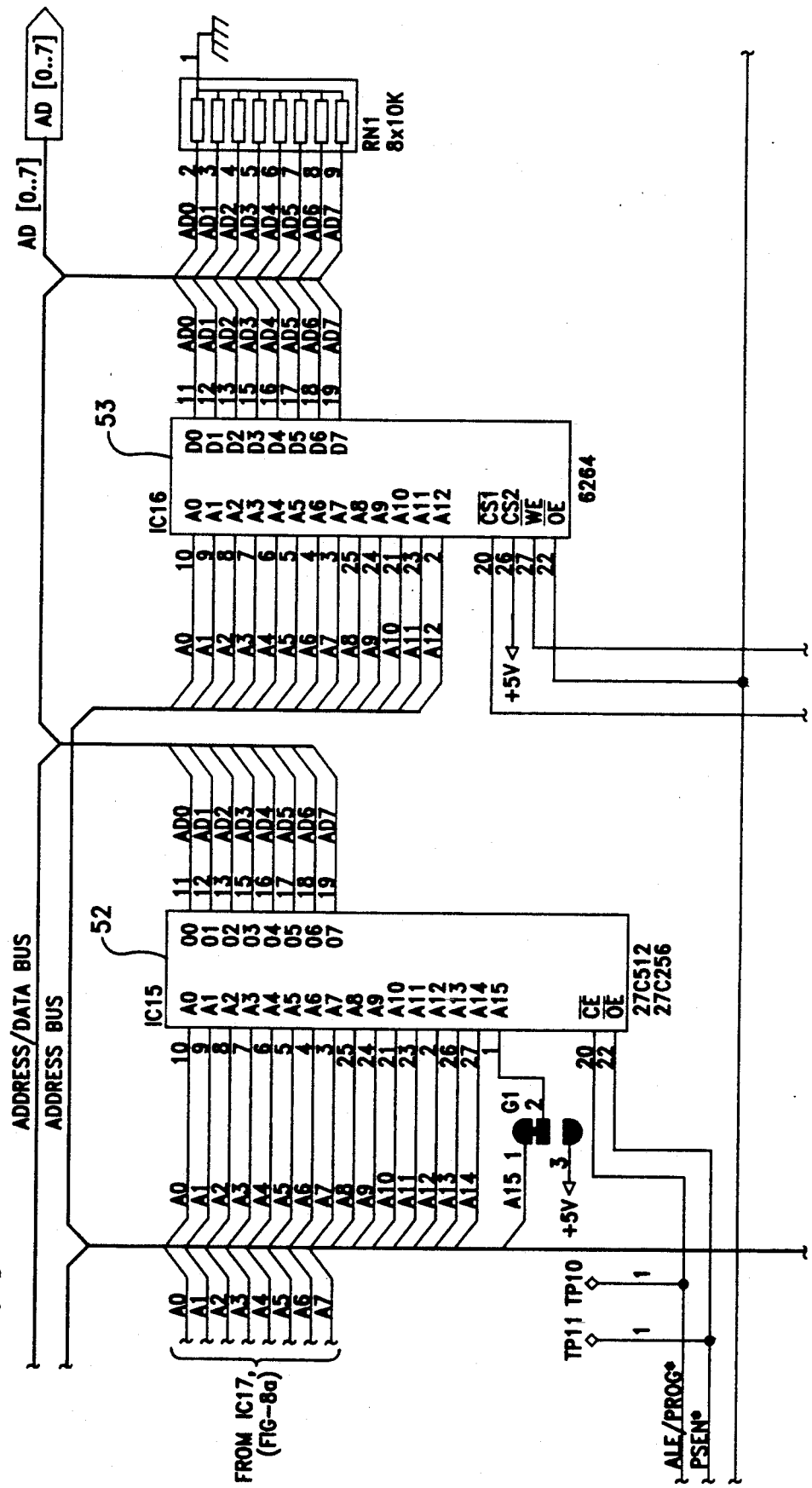

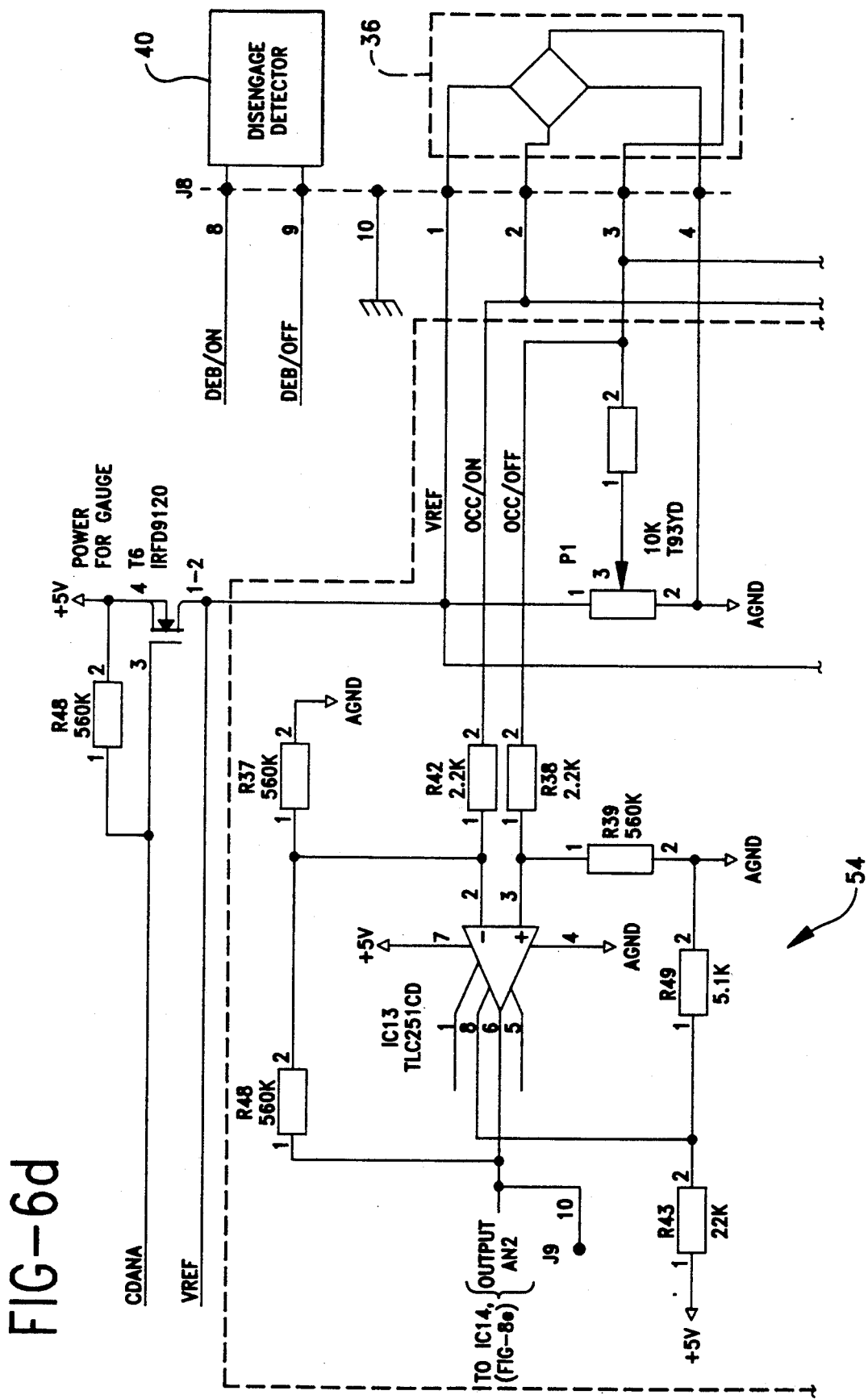

METHOD AND APPARATUS FOR DETERMINING PRESSURE AND DETECTING OCCLUSIONS IN A SYRINGE PUMP

BACKGROUND

1. Field of the Invention

The invention relates generally to the detection of occlusions in the infusion line of a syringe pump. In particular, the invention relates to a programmable syringe pump which utilizes a novel algorithm to determine whether an occlusion exists in the infusion line.

2. Background of the Invention

A syringe pump is a device for pumping fluid from a syringe into a patient. The syringe is placed in the pump and connected to the patient via an infusion line. During the course of infusing medication into a patient, it is possible for an occlusion to arise in the infusion line. Such a condition, if undetected may cause injury to the patient.

An occlusion in the infusion line will cause the force between the pusher of the syringe pump and the syringe plunger to increase due to increased pressure in the syringe. In the prior art, an occlusion in the infusion line has been detected by a pre-loaded spring which collapses when the force between the pusher of the syringe pump and the plunger increases beyond the predetermined force in the spring. This in turn triggers a switch which alerts the user or shuts off the syringe pump.

More sophisticated syringe pumps monitor the force between the pusher and the plunger by means of a force transducer. The amount of force increase in the syringe corresponding to an occlusion requiring remedial action varies from one syringe to another. For this reason, the force is translated into a pressure. This translation takes into account the frictional force in the syringe and the cross-sectional area of the syringe by use of the formula:

$$P = \frac{F - Ff}{A}$$

where
P = the liquid pressure in the syringe
F = the pushing force measured by the transducer
Ff = the frictional force in the syringe
A = the cross sectional area of the syringe The frictional force in the syringe and the cross sectional area of the syringe are assumed to be constant. However, in reality (1) the frictional force in the syringe is not constant and varies with pressure; and (2) The cross sectional area of the syringe may also vary with pressure. The prior art force to pressure conversion is there not very accurate.

SUMMARY OF THE INVENTION

The invention is a syringe pump having a transducer to detect the force exerted on the plunger of the syringe. The detected force is used to calculate the pressure in the syringe by means of an algorithm which compensates for the frictional force in the syringe and scales the detected force by an empirically derived scaling factor. The scaling factor is determined by measuring the force on the plunger when the pressure in the syringe is at a predetermined value. Because the scaling factor is obtained from force and pressure measurements, there is no need to consider the cross sectional area of the syringe and the actual (and variable) frictional force in the syringe.

The calculated pressure may then be compared with a predetermined occlusion pressure. Remedial action may be taken if the calculated pressure exceeds the predetermined occlusion pressure.

The scaling factor varies depending on the type of syringe used. The invention thus permits a variety of types of syringes to be used in the syringe pump by storing syringe type-dependent parameters in a memory and calculating the pressure in the syringe. The invention also results in far more accurate pressure readings than were available using the prior art, because cross sectional area and the actual frictional force are not used in the algorithm.

BRIEF DESCRIPTION OF THE DRAWINGS

FIG. 2 is a perspective view of the drive mechanism of the syringe pump;

FIG. 6a–e are schematic diagrams of the main electronic components of the invention.

DETAILED DESCRIPTION

Figure 1:
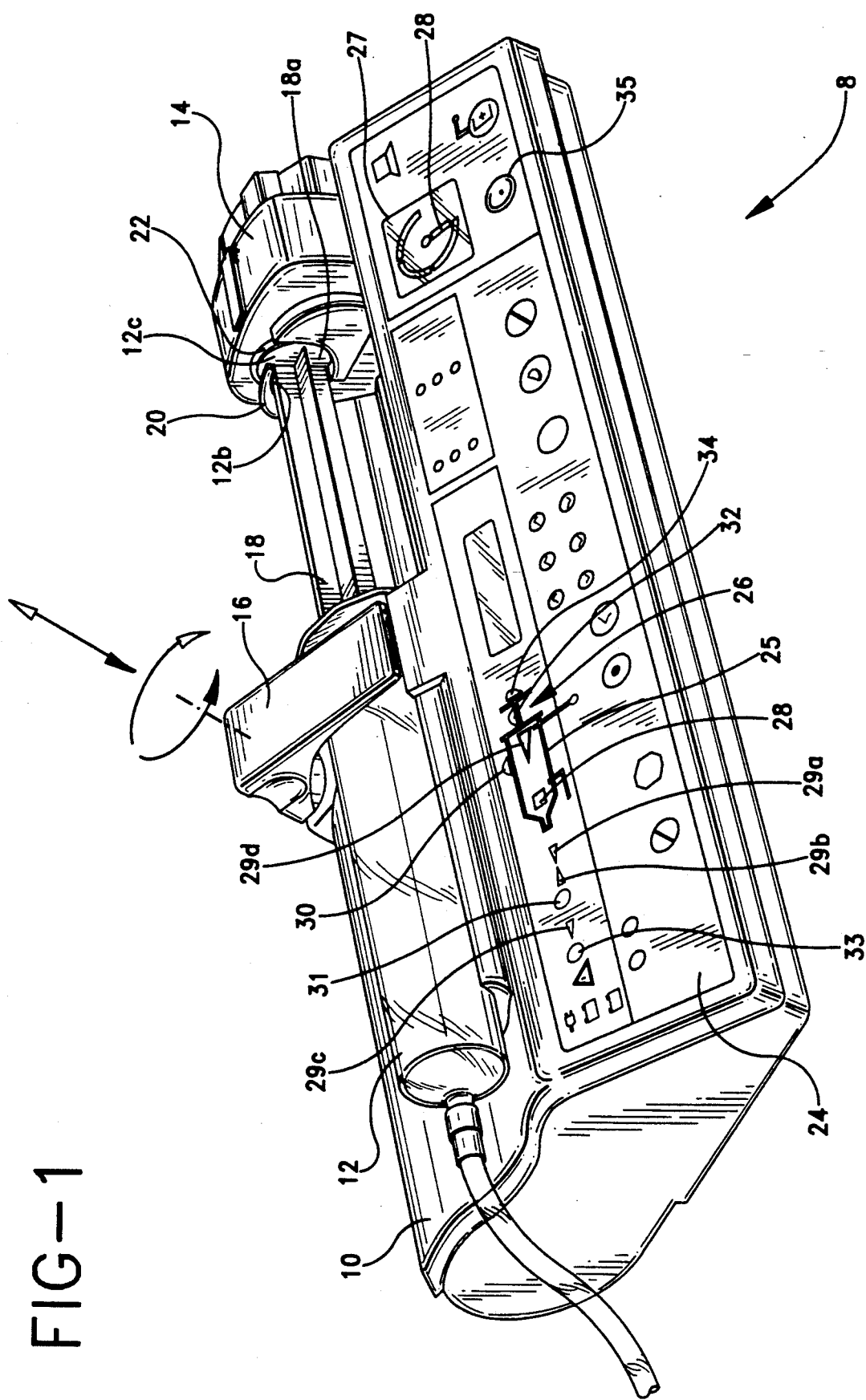
FIG. 1 is a perspective view of a syringe pump embodying the invention.

A syringe pump 8 embodying the invention is shown in FIG. 1. Housing 10 supports syringe 12, pusher 14 and syringe clamp 16. Syringe clamp 16 holds syringe 12 in place on housing 10. Plunger 18 of syringe 12 is pushed by pusher 14 which is driven by an electric motor via a lead screw (see FIG. 2).

Pusher 14 is provided with antisiphon catch 20 which engages flange 18a of plunger 18, thus preventing plunger 18 from moving independently of pusher 14. Pusher 14 is against flange 18a thereby pumping fluid from syringe 12.

FIG. 2 shows the chassis and mechanical components of pump 8. Chassis 226 carries motor 230 and lead screw 222. Motor 230 drives lead screw 222 via gear assembly 232. Pusher 14 is driven by the interaction of pusher block 228 with lead screw 222. Pusher block contains half nuts 322, 324 which interact with lead screw 222 (see FIG. 3).

Figure 5:
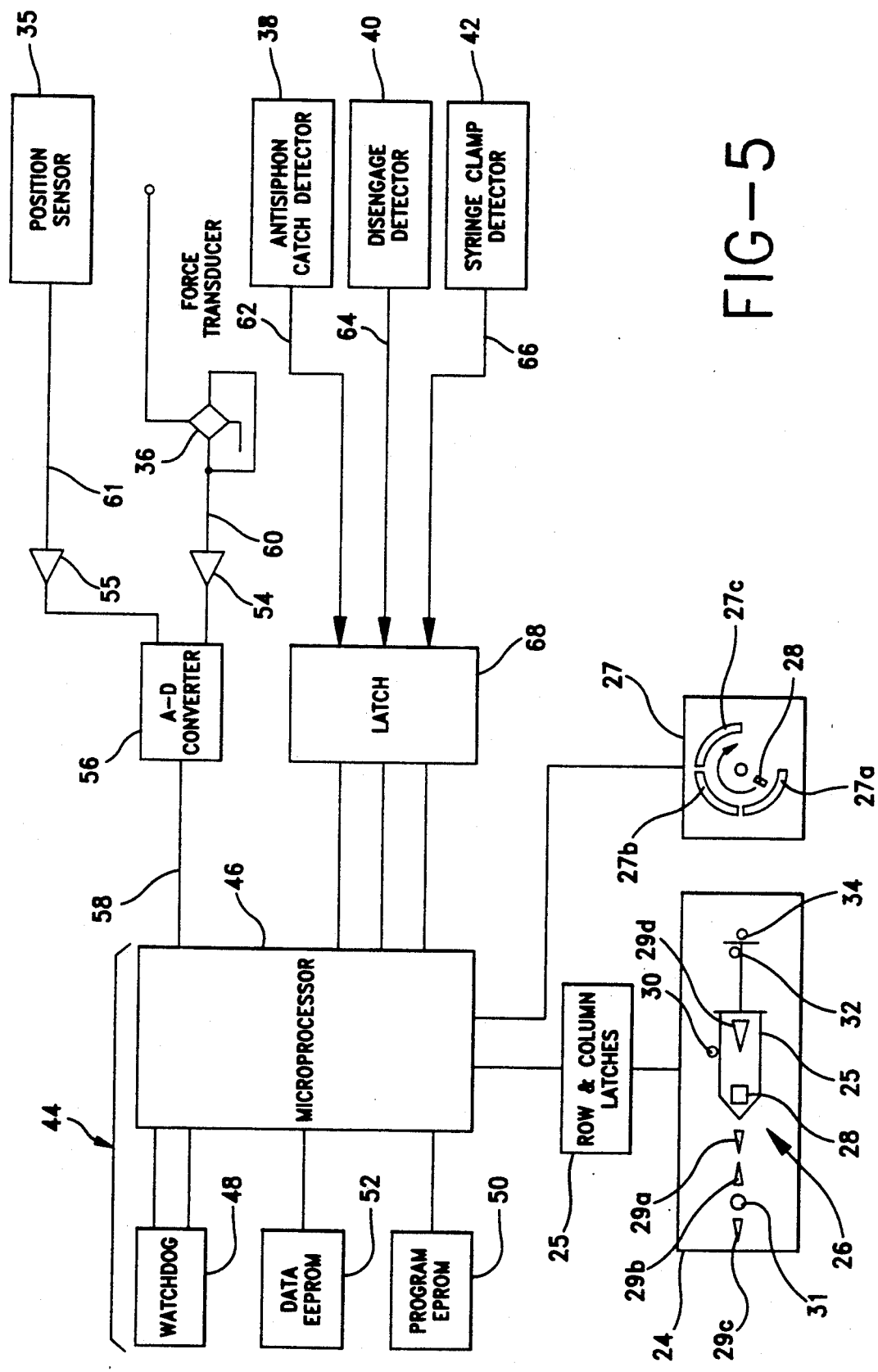
FIG. 5 is a block diagram of the electronic components of the invention.

FIG. 5 is a block diagram showing the main electronic components of the invention. Transducers are provided to detect various parameters of the syringe pump which are displayed on panel 24. The transducers are: force transducer 36, antisiphon catch detector 38, disengage detector 40 and syringe clamp detector 42. The outputs of these transducers 60, 62, 64 and 66 respectively are fed into central processing unit 44 via various signal processing modules. Schematic diagrams of the various electronics modules are shown in FIGS. 8a. The values and types of the components are indicated on the schematic diagrams.

Figure 6A:
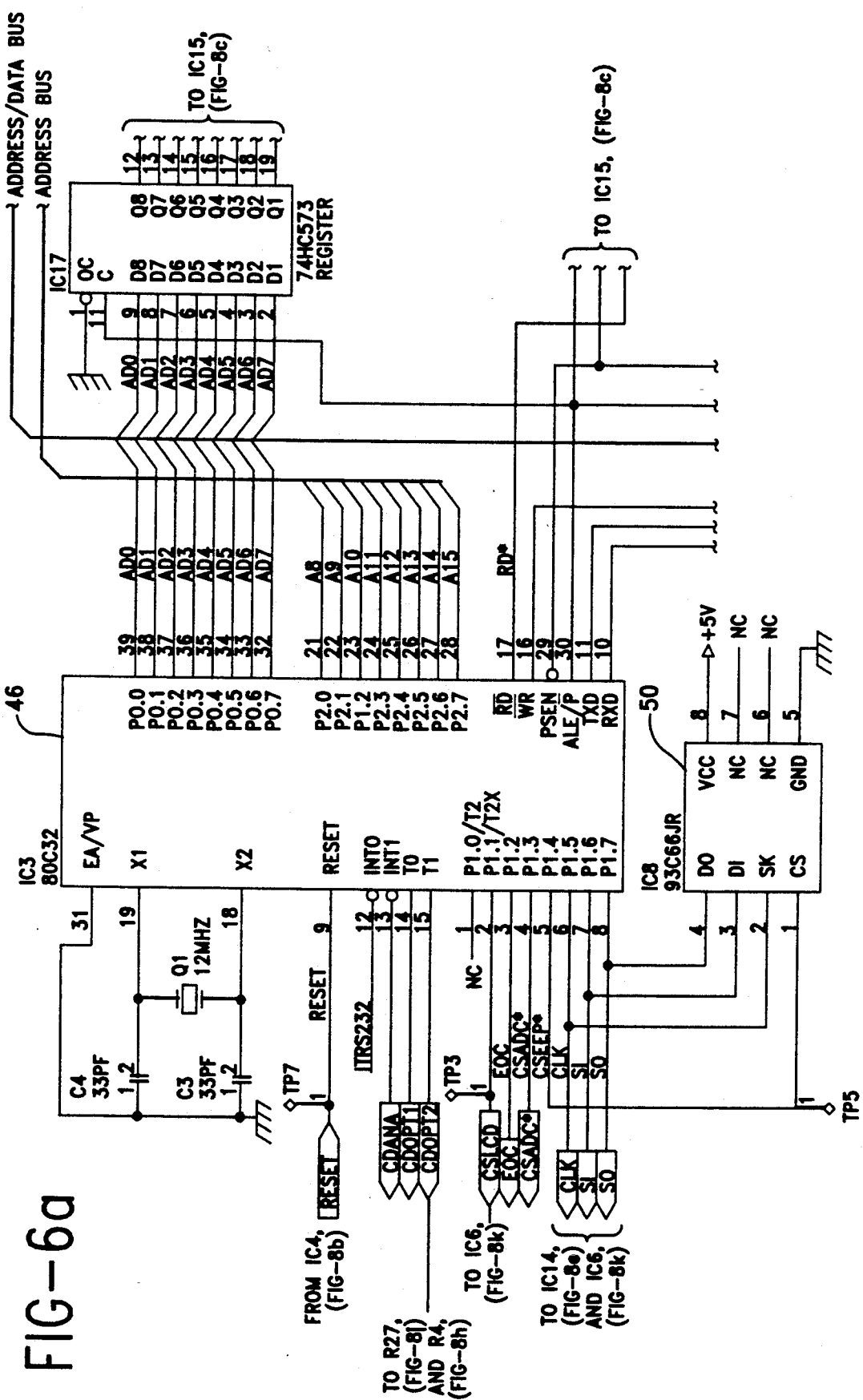

Central processing unit 44 comprises microprocessor 46 (FIG. 6a) with random access memory 53 (FIG. 8a), watchdog 48 (FIG. 6b), EPROM 50 (FIG. 6a) and EEPROM 52 (FIG. 6c). Watchdog 48 monitors microprocessor 46 to ensure its proper operation. EEPROM 52 contains data concerning the parameters of the syringes used in the pump. EPROM 50 contains a software program which controls the operation of the syringe pump.

Figure 6E:
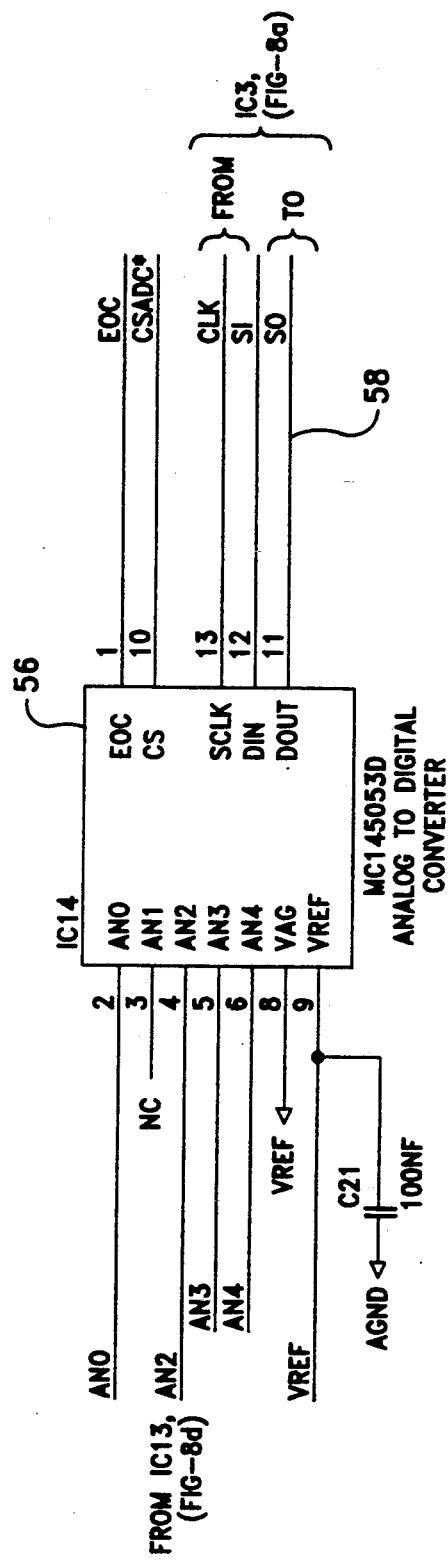

The output of force transducer 36 is conditioned by signal conditioning circuit 54 (FIG. 6d), which converts the output of force transducer 36 into a form suitable for input into analog to digital converter 56 (FIG. 6e). Analog to digital converter 56 digitizes the analog output and produces serial output 58 which is in turn fed into input port 60 of microprocessor 46.

Figure 4:
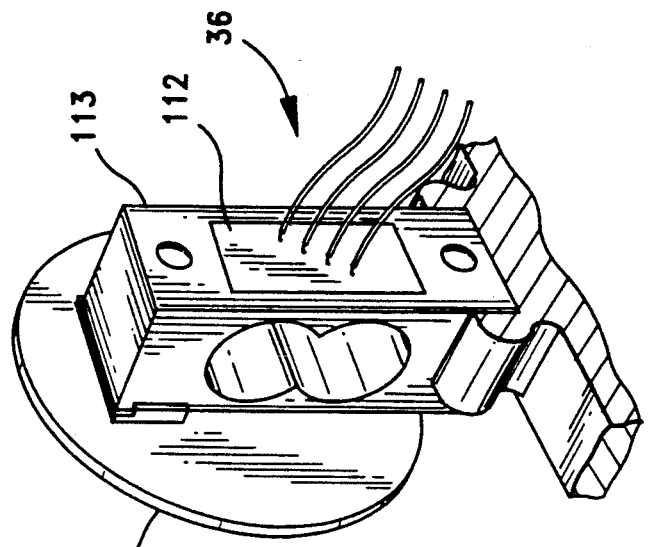
FIG. 4 is a perspective view of the pusher disc and force transducer.

FIG. 4 shows force transducer 36 in greater detail. Force transducer 36 is made up of four strain gauges in a wheatstone bridge configuration. The bridge has an impedance of 350 ohms or 1 Kohm with a tolerance of $\pm 15\%$. The range of force measurements is 0 to 150 N. The bridge sensitivity is 1.7 mV/V to 2.4 mV/V under a load of 150 N at 20 degrees centigrade. The bridge is powered intermittently under the control of microprocessor 46 (line CDANA in FIGS. 6a and 6d) in order to conserve energy.

Figure 3:
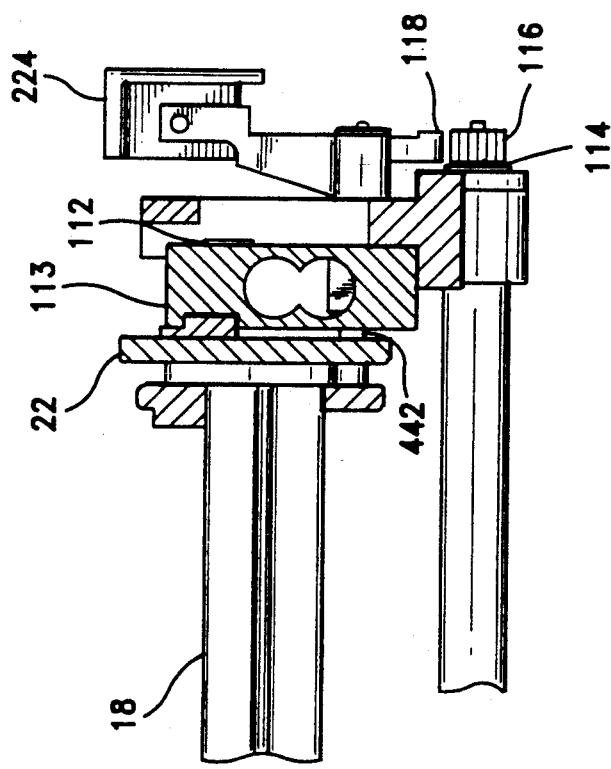
FIG. 3 is a cross sectional view of the pusher mechanism of the invention.

As seen in FIGS. 3 and 4, strain gauges 112 are glued onto beam 114. When force is applied to pressure plate 22, beam 114 flexes, causing strain gauges 112 to distort and produce output 60.

Output 60 of force transducer 36 is fed into conditioning module 54 (FIG. 6d) and thereafter into analog to digital converter 56 which converts the conditioned output of force detector 36 into serial output 58. Serial output 58 is then fed into input 60 of microprocessor 46.

Resident in EPROM 50 is a software program for microprocessor 46 which calculates the pressure inside syringe 12 continuously as the force on the plunger 18 is measured by force transducer 36. Certain parameters which are used by the program to calculate the pressure in the syringe and stored in EPROM 52. Since syringe pump 8 is programmable to accommodate various types of syringe, a set of parameters for each type of syringe, is stored in EPROM 52.

The parameters stored in EEPROM 52 include:
Ff=average frictional force between the syringe plunger and the syringe barrel at null (atmospheric) pressure.
Pc=the pressure in the syringe when a calibration force is applied to the plunger. The calibration force is typically 5 kgF and leads to a value of Pc of around 0.7 bar, a usual pressure threshold.
Fc=the force with which the plunger is loaded to obtain a pressure of Pc in the syringe.

The program in EPROM 50 is used by microprocessor 46 to calculate the pressure in the syringe. Microprocessor 46 then compares the calculated pressure with a pressure value or values stored in EEPROM 52 for that syringe. If the calculated pressure exceeds the stored pressure, an occlusion alarm is generated by microprocessor 46.

The algorithm for calculating the pressure in the syringe is:

$$P = \frac{(F - Ff)}{Fc - Ff} \cdot Pc$$

where F is the force measured by force transducer 36 and Fc, Ff and Pc are the parameters defined above.

The main advantages of this formula over the traditional formula described in the BACKGROUND section above are (1) it is not highly dependent on the frictional force in the syringe which is known to vary with pressure and (2) that the cross sectional area of the syringe need not be determined. Rather, the pressure in the syringe is calculated using parameters which are easy to determine empirically.

It can be demonstrated mathematically that this formula results in a smaller error in the calculation of pressure than results from the prior art formula.

In the prior art Ff is considered to be constant, the force required to move the plunger without pressure application of the formula $$P = \frac{F - Ff}{A}$$

results in:

$$P\text{measured} = \frac{F - Ffo}{A} \tag{1}$$

Ffo is the frictional force in the syringe, measured at null differential pressure.

However, friction is a function of pressure and can be expressed as $$Ff(P) = Ffo + kP \tag{2}$$

where k is a constant for a particular syringe dependent on the geometry and materials of the syringe.

Assuming the cross-sectional area is known accurately the actual pressure in the syringe is given by using equation (2) in the formula $$P = \frac{F - Ff}{A}$$

$$P\text{actual} = \frac{F - Ffo - kp}{A}. \tag{3}$$

The difference between the actual pressure from equation (3) and the predicted pressure from equation (1) is $$\Delta p = \frac{kp}{A}.$$

The error per unit of pressure using the prior art formula is $$\frac{\Delta p}{p} = \frac{k}{A} \tag{4}$$

Applying the formula of the invention $$P\text{ measured} = \frac{(F - Ffo)}{(Fc - Ffo)} Pc \tag{5}$$

In order to evaluate the error resulting from the use formula (5), the actual pressure can be expressed in a suitable manner:

Equation (3) is still valid when F=Fc. In this case, P=Pc, thus generating the equation:

$$Pc = \frac{Fc - Fpo - Pcp}{A} \tag{6}$$

Eliminating A in equations (3) and (6) gives:

$$P\text{actual} = \frac{(F - Fpo - Pcp)}{(Fc - Fpo - Pcp)} Pc \tag{7}$$

-continued and then $$P\text{actual} = \frac{(F - F_{fo})\left[1 - \frac{kp}{F - F_{fo}}\right]}{(F_c - F_{fo})\left[1 - \frac{kp}{F_c - F_{fo}}\right]} P_c \quad (8)$$

Since $$\frac{kp}{F - F_{po}} \text{ and } \frac{kp}{F_{po}}$$

are very small in comparison with 1, equation (8) can be approximated by:

$$P\text{actual} \simeq \frac{F - F_{fo}}{F_c - F_{fo}} P_c \left[1 - \frac{kp}{F - F_{Po}} + \frac{kp}{F - F_p}\right] \quad (9)$$

The difference between the measured and actual values is then:

$$\Delta p = P\text{measured } kp \left[\frac{1}{F_c - F_p} - \frac{1}{F - F_p}\right] \quad (10)$$

and the error per unit of pressure:

$$\Delta p = P\text{measured } k \left[\frac{1}{F_c - F_p} - \frac{1}{F - F_p}\right] \quad (11)$$

Substituting typical values for a 60 cc syringe into equations (4) (prior art) and (11) (present invention) results in:

Prior art $\frac{\Delta p}{p} = \frac{k}{5.55}$

Present invention $\frac{\Delta p}{p} = \frac{k}{13,5}$ where Ffo=10N
Fc=50N
A=5.55 cm²
Pmeasured=0.4 bar
F≃33N Thus it can be seen that the error in the pressure measurement using the present invention is substantially reduced in comparison to that of the prior art.

We claim:

1. A method of determining the pressure in a syringe used in a syringe pump comprising the steps of:
   measuring the force on the plunger of the syringe;
   subtracting a predetermined frictional force (Ff) in the syringe from the measured force to produce a scaled force;
   multiplying the scaled force by a correction factor dependent on a predetermined calibration pressure (Pc), the predetermined frictional force (Ff) and a predetermined calibration force (Fc).

2. The method of claim 1 wherein Ff, Fc and Pc are empirically derived.

3. The method of claim 1 wherein the correction factor is obtained by dividing Pc by the difference between Fc and Ff.

4. The method of claim 2 wherein Fc is determined by measuring the force on the plunger of the syringe when a pressure of Pc exists in the syringe.

5. The method of claim 2 wherein Pc is determined by measuring the pressure in the syringe when a force of Fc is applied to the plunger of the syringe.

6. The method of claim 2 wherein Ff is the frictional force between the wall of the syringe and the stopper of the syringe when the pressure inside the syringe is the same as ambient pressure.

7. The method of claim 1 further comprising the step of comparing the pressure with a threshold pressure determined to determine whether an occlusion has occurred in the syringe pump.

8. A syringe pump for pumping fluid from a syringe having a plunger, a stopper and a wall, the syringe pump comprising:
   means for detecting the force on the plunger;
   means for converting the force into a calculated pressure using an algorithm;
   means for storing predetermined pressure values;
   means for comparing the calculated pressure with a predetermined pressure value;
   means for informing a user if the calculated pressure exceeds the predetermined value with which the calculated pressure was compared;
   wherein the algorithm calculates the calculated pressure by subtracting a frictional force from the detected force, multiplying result by a calibration pressure divided by the difference between a calibration force and the frictional force.

* * * * *